(12) United States Patent
Jokaji et al.

(10) Patent No.: US 12,329,929 B2
(45) Date of Patent: Jun. 17, 2025

(54) FILTRATION DEVICE

(71) Applicant: TERUMO KABUSHIKI KAISHA, Tokyo (JP)

(72) Inventors: Mitsuru Jokaji, Minami-Alps (JP); Takeshi Toyama, Minami-Alps (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 854 days.

(21) Appl. No.: 17/471,065

(22) Filed: Sep. 9, 2021

(65) Prior Publication Data

US 2021/0402086 A1    Dec. 30, 2021

Related U.S. Application Data

(63) Continuation of application No. PCT/JP2020/002943, filed on Jan. 28, 2020.

(30) Foreign Application Priority Data

Mar. 12, 2019  (JP) ................................. 2019-045139

(51) Int. Cl.
*A61M 5/165*    (2006.01)
*A61M 5/38*    (2006.01)

(52) U.S. Cl.
CPC .............. *A61M 5/165* (2013.01); *A61M 5/38* (2013.01); *A61M 2005/1652* (2013.01); *A61M 2207/00* (2013.01)

(58) Field of Classification Search
CPC .................... A61M 5/165; A61M 5/38; A61M 2005/1652; A61M 2207/00;
(Continued)

(56) References Cited

U.S. PATENT DOCUMENTS 4,190,426 A * 2/1980 Ruschke ................. A61M 5/36
96/219
4,422,939 A  12/1983 Sharp et al.
(Continued)

FOREIGN PATENT DOCUMENTS

CN     1131577 A    9/1996
CN     1195301 A    10/1998
(Continued)

OTHER PUBLICATIONS

Machine generated translation of JP-2018164649-A (Year: 2018).*
(Continued)

*Primary Examiner* — Magali P Slawski
*Assistant Examiner* — Bernadette Karen McGann
(74) *Attorney, Agent, or Firm* — Foley & Lardner LLP

(57) ABSTRACT

A filtration device includes: a housing that defines a liquid flow path; and a filtration sheet that separates the liquid flow path into a flow path upstream side and a flow path downstream side. The housing includes: a first housing member and a second housing member that sandwich the filtration sheet, and a joining member that joins the first housing member and the second housing member in a state in which the filtration sheet is sandwiched between the first housing member and the second housing member. A gap is located between the first housing member and the second housing at a position outward of an outer edge of the filtration sheet. The joining member seals the gap between the first housing member and the second housing member at the position outward of the outer edge of the filtration sheet.

8 Claims, 4 Drawing Sheets

(58) Field of Classification Search
CPC ........ A61M 1/3635; A61M 2005/1657; A61M 2205/7527; A61M 2205/7545
See application file for complete search history.

(56) References Cited

U.S. PATENT DOCUMENTS

| | | |
|---|---|---|
| 5,476,587 A | 12/1995 | Kuroki et al. |
| 5,707,520 A | 1/1998 | Kuroki et al. |

FOREIGN PATENT DOCUMENTS

| | | | | |
|---|---|---|---|---|
| CN | 206534951 U | 10/2017 | | |
| CN | 207462404 U | 6/2018 | | |
| CN | 207856029 U | 9/2018 | | |
| DE | 27 04 099 A1 | 9/1977 | | |
| DE | 38 01 866 A1 | 8/1989 | | |
| DE | 10 2005 052 486 A1 | 5/2007 | | |
| DE | 10 2011 120 646 A1 | 6/2013 | | |
| EP | 0 325 712 A1 | 8/1989 | | |
| EP | 806475 A2 * | 11/1997 | .......... | A61M 1/3633 |
| JP | S53-165796 U | 12/1978 | | |
| JP | S59-67966 A | 4/1984 | | |
| JP | S60-193468 A | 10/1985 | | |
| JP | S60-194959 A | 10/1985 | | |
| JP | H01-17383 B2 | 3/1989 | | |
| JP | 2018164649 A * | 10/2018 | | |
| WO | WO-2014/107436 A1 | 7/2014 | | |
| WO | WO-2015-050215 A1 | 4/2015 | | |
| WO | WO-2017/141948 A1 | 8/2017 | | |

OTHER PUBLICATIONS

First Chinese Office Action issued in connection with CN Appl. Ser. No. 202080006078.8 dated Jul. 26, 2022.
Written Opinion of the International Search Authority, dated Apr. 14, 2020, issued in corresponding International Application No. PCT/JP2020/002943 (9 pages).
International Searching Authority, "International Search Report," issued in connection with International Patent Application No. PCT/JP2020/002943, dated Apr. 14, 2020.
International Searching Authority, "Written Opinion," issued in connection with International Patent Application No. PCT/JP2020/002943, dated Apr. 14, 2020.
Extended European Search Report in EP Appl. No. 20770356.2, dated Feb. 16, 2022 (6 pages).

* cited by examiner

FILTRATION DEVICE

CROSS-REFERENCE TO RELATED APPLICATIONS

This application is a bypass continuation of PCT Application No. PCT/JP2020/002943, filed on Jan. 28, 2020, which claims priority to Japanese Application No. 2019-045139, filed on Mar. 12, 2019. The contents of these applications are hereby incorporated by reference in their entireties.

BACKGROUND

The present disclosure relates to a filtration device.

Currently, various types of medical filtration devices are used to remove foreign matters in a liquid. JP-B-H1-17383 ("JP '383") describes such a filtration device. The filtration device described in JP '383 includes a hydrophilic filter as a filtration sheet.

WO-2015-050215 ("WO '215") discloses a blood processing filter as a filtration device. The blood processing filter of WO '215 includes an inlet side container member and an outlet side container member. An inlet side joint portion and an outlet side joint portion, which are joined to each other to form a joint portion, are respectively provided on outer edge portions including end surfaces of the inlet side container member and the outlet side container member according to WO '215. The inlet side container member and the outlet side container member are respectively provided with an inlet side grip portion and an outlet side grip portion at inner edges of the inlet side joint portion and the outlet side joint portion. The inlet side grip portion and the outlet side grip portion grip an outer edge portion of a filter element as a filtration sheet.

SUMMARY

The hydrophilic filter as the filtration sheet described in JP '383 is supported on a housing. On the other hand, the filter element as the filtration sheet described in WO '215 is gripped by the inlet side grip portion and the outlet side grip portion. Therefore, the filter element described in PTL2 is less likely to be displaced. However, there is still room for improvement in fixing strength of the filtration sheet.

An object of the present disclosure is to provide a filtration device having a configuration capable of fixing a filtration sheet more firmly.

A filtration device according to a first aspect of the present disclosure includes: a housing that defines a liquid flow path; and a filtration sheet that separates the liquid flow path into a flow path upstream side and a flow path downstream side. The housing includes a first housing member and a second housing member that sandwich the filtration sheet, and a joining member that joins the first housing member and the second housing member in a state in which the filtration sheet is sandwiched between the first housing member and the second housing member. The first housing member and the second housing member are not in contact with each other at a position on an outer side relative to an outer edge of the filtration sheet. The joining member seals a gap between the first housing member and the second housing member at the position on the outer side relative to the outer edge of the filtration sheet.

In one embodiment of the present disclosure, the joining member is located in the gap between the first housing member and the second housing member, and is joined to the first housing member and the second housing member.

In one embodiment of the present disclosure, the filtration sheet includes an outer edge portion located on an outer side relative to a sandwiched portion sandwiched by the first housing member and the second housing member in a plan view in a thickness direction, and the joining member is joined to the outer edge portion of the filtration sheet.

In one embodiment of the present disclosure, at least one member of the first housing member and the second housing member includes a protruding portion protruding toward the other member, and the filtration sheet is sandwiched between the first housing member and the second housing member at a position of the protruding portion.

In one embodiment of the present disclosure, the filtration sheet is a hydrophilic filter.

In one embodiment of the present disclosure, the first housing member defines an opening portion capable of discharging a gas in the liquid flow path, and the filtration device further includes a ventilation sheet that covers the opening portion.

In one embodiment of the present disclosure, the first housing member defines one of a liquid inflow port and a liquid outflow port of the liquid flow path, and the second housing member defines the other one of the liquid inflow port and the liquid outflow port of the liquid flow path.

According to the present disclosure, it is possible to provide a filtration device having a configuration capable of fixing a filtration sheet more firmly.

DETAILED DESCRIPTION

Figure 1:
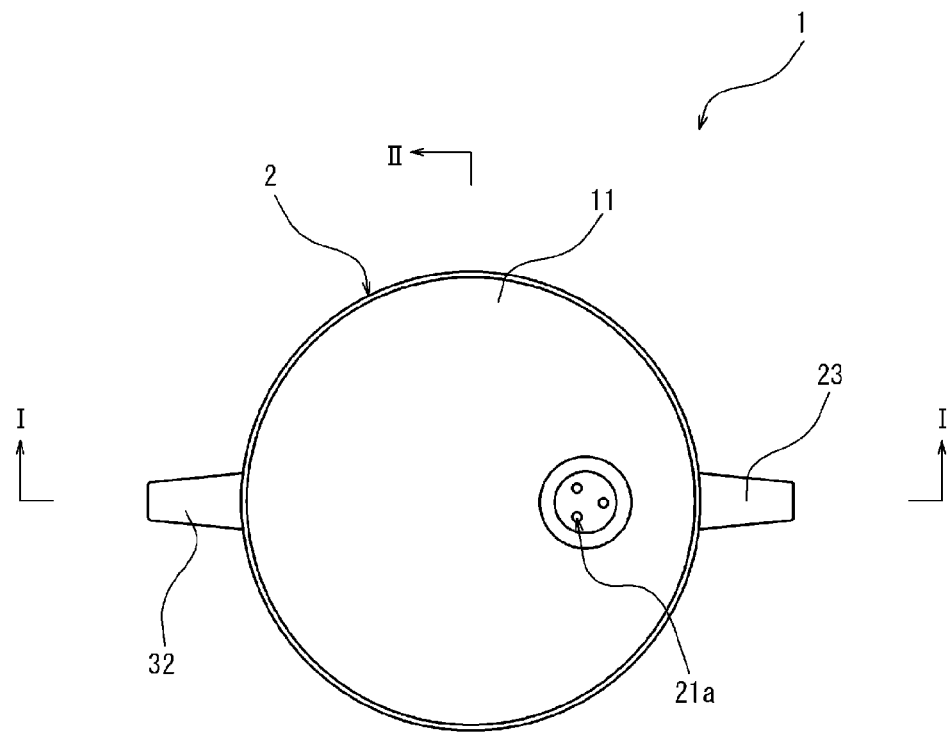
FIG. 1 is a top view of a filtration device according to an embodiment of the present disclosure.
Figure 1:
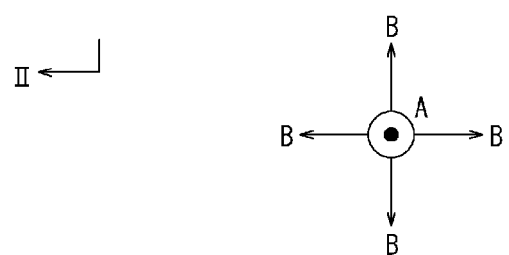

Hereinafter, an embodiment of a filtration device according to the present disclosure will be described as an example with reference to the drawings. In the drawings, common members and portions are denoted by the same reference numerals.

The filtration device according to the present disclosure can be used as a medical filtration device. Examples of the medical filtration device include a filtration device for infusion, a filtration device for hemodialysis, and a filtration device for removing white blood cells. Hereinafter, in the present embodiment, the filtration device for infusion will be described as an example of the medical filtration device.

Figure 2:
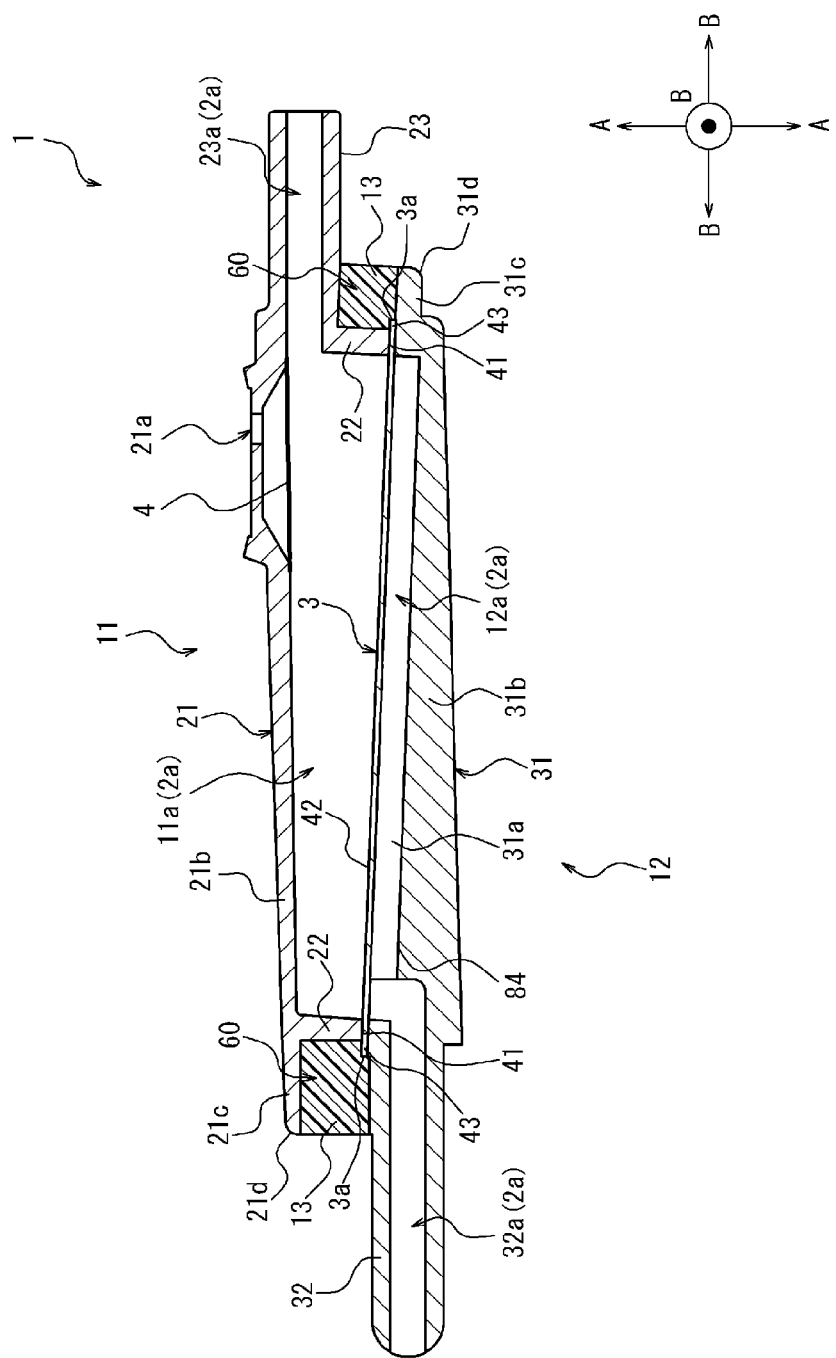
FIG. 2 is a cross-sectional view taken along a line I-I in FIG. 1.
Figure 3:
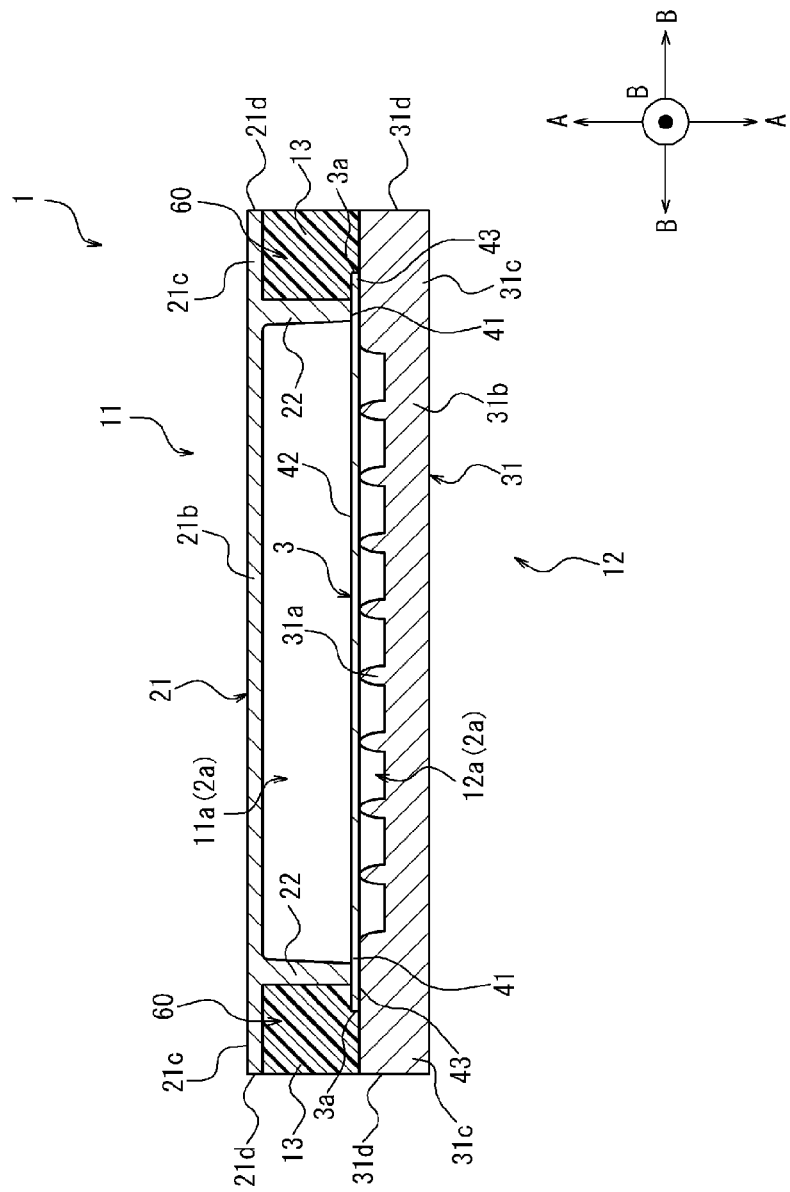
FIG. 3 is a cross-sectional view taken along a line II-II in FIG. 1.

FIG. 1 shows a filtration device 1 for infusion as an embodiment of the filtration device according to the present disclosure. FIG. 1 is a top view of the filtration device 1. FIGS. 2 and 3 are cross-sectional views of the filtration device 1. FIG. 2 is a cross-sectional view of a cross section taken along a line I-I in FIG. 1. FIG. 3 is a cross-sectional view of a cross section taken along a line II-II in FIG. 1.

As shown in FIGS. 1 to 3, the filtration device 1 includes a housing 2 and a filtration sheet 3. Hereinafter, a thickness direction of the filtration sheet 3 is simply referred to as a "thickness direction A". A direction orthogonal to the thickness direction of the filtration sheet 3 is simply referred to as a "sheet extending direction B".

As shown in FIGS. 2 and 3, the housing 2 defines a liquid flow path 2a. The filtration sheet 3 separates the liquid flow path 2a into a flow path upstream side and a flow path downstream side.

Foreign matters in a liquid flowing through the liquid flow path 2a from the flow path upstream side toward the flow path downstream side is removed by passing through the filtration sheet 3. That is, the filtration sheet 3 is a filter that removes the foreign matters in the liquid.

As shown in FIGS. 2 and 3, the housing 2 includes a first housing member 11, a second housing member 12, and a joining member 13. The first housing member 11 and the second housing member 12 sandwich the filtration sheet 3. The joining member 13 joins the first housing member 11 and the second housing member 12 in a state in which the filtration sheet 3 is sandwiched between the first housing member 11 and the second housing member 12.

As shown in FIGS. 2 and 3, the first housing member 11 and the second housing member 12 are not in contact with each other at a position on an outer side relative to an outer edge 3a of the filtration sheet 3 in the sheet extending direction B. That is, although the first housing member 11 and the second housing member 12 sandwich the filtration sheet 3 from both surfaces in the thickness direction A, the first housing member 11 and the second housing member 12 are not in direct contact each other at a position at which the filtration sheet 3 is not interposed between the first housing member 11 and the second housing member 12.

As shown in FIGS. 2 and 3, the joining member 13 seals a gap 60 between the first housing member 11 and the second housing member 12 at the position on the outer side relative to the outer edge 3a of the filtration sheet 3 in the sheet extending direction B. That is, when joining the first housing member 11 and the second housing member 12, the joining member 13 seals the gap 60 between the first housing member 11 and the second housing member 12 at the position on the outer side relative to the outer edge 3a of the filtration sheet 3 in the sheet extending direction B.

As described above, because the filtration sheet 3 is sandwiched between the first housing member 11 and the second housing member 12 which are not in direct contact with each other, the fixing strength of the filtration sheet 3 can be increased as compared with a configuration in which the first housing member and the second housing member are in direct contact with each other and positioned with each other. The first housing member 11 and the second housing member 12 in the state of sandwiching the filtration sheet 3 are joined by the joining member 13 on the outer side relative to the outer edge 3a of the filtration sheet 3 in the sheet extending direction B. Accordingly, a mutual positional relationship between the first housing member 11 and the second housing member 12 can be fixed by the joining member 13 while maintaining the state in which the filtration sheet 3 is sandwiched by the first housing member 11 and the second housing member 12. Accordingly, it is possible to implement the housing 2 capable of increasing the fixing strength of the filtration sheet 3.

Hereinafter, further details of the filtration device 1 according to the present embodiment will be described with reference to FIGS. 1 to 3. The filtration device 1 of the present embodiment includes a ventilation sheet 4 in addition to the housing 2 and the filtration sheet 3 described above.

[Housing 2]

As described above, the housing 2 of the present embodiment includes the first housing member 11, the second housing member 12, and the joining member 13.

The first housing member 11 of the present embodiment includes a top plate portion 21, an annular protruding portion 22 protruding from the top plate portion 21, and an inflow port portion 23 protruding radially outward from the annular protruding portion 22.

The top plate portion 21 has a substantially circular flat external shape. The top plate portion 21 includes a central portion 21b on a radially inner side relative to a position in which the annular protruding portion 22 protrudes, and an outer edge portion 21c on a radially outer side relative to the position in which the annular protruding portion 22 protrudes.

The top plate portion 21 defines an opening portion 21a through which gas in the liquid flow path 2a can be discharged to the outside. Specifically, the opening portion 21a of the present embodiment is provided in the central portion 21b of the top wall portion 21. A lower surface side of the opening portion 21a, which is the liquid flow path 2a side, is covered with the ventilation sheet 4 described later.

The annular protruding portion 22 protrudes from a lower surface of the top plate portion 21 toward the second housing member 12. As will be described in detail later, the filtration sheet 3 of the present embodiment is sandwiched and compressed between a distal end surface of the annular protruding portion 22 and an upper surface of the second housing member 12 to be described later.

The inflow port portion 23 is a tubular portion protruding radially outward from the annular protruding portion 22, and defines a liquid inflow port 23a inside. The liquid inflow port 23a communicates with a flow path upstream side space 11a defined by the central portion 21b of the top plate portion 21 and the protruding portion 22. In other words, the liquid inflow port 23a and the flow path upstream side space 11a constitute a part of the liquid flow path 2a in the housing 2.

The second housing member 12 of the present embodiment includes a main body plate portion 31 and an outflow port portion 32 protruding from the main body plate portion 31.

The main body plate portion 31 has a substantially circular flat external shape. The main body plate portion 31 includes a central portion 31b formed with a plurality of ribs 31a on an upper surface 84 of the main body plate portion 31 facing the lower surface of the top plate portion 21 of the first housing member 11, and an outer edge portion 31c formed with no ribs 31a on the upper surface 84 of the main body plate portion 31.

The ribs 31a formed in the central portion 31b extend substantially linearly. Extending directions of the plurality of ribs 31a are substantially parallel to each other. The plurality of ribs 31a are disposed at predetermined intervals. The filtration sheet 3 is supported by top portions of the plurality of ribs 31a. Then, the liquid that has passed through the filtration sheet 3 flows into a groove space as a flow path downstream side space 12a among the plurality of ribs 31a.

The outer edge portion 31c, together with the annular protruding portion 22 of the first housing member 11, constitutes a sandwiching portion that sandwiches the filtration sheet 3. Specifically, the filtration sheet 3 is sandwiched between the distal end surface of the annular protruding portion 22 of the first housing member 11 and an upper surface of the outer edge portion 31c of the main body plate portion 31 of the second housing member 12. In the present embodiment, the upper surface of the outer edge portion 31c is flush with a virtual plane passing through the top portions of the plurality of ribs 31a of the central portion 31b.

The outflow port portion 32 is a tubular portion protruding in a radially outward side of the main body plate portion 31, and defines a liquid outflow port 32a inside. The liquid outflow port 32a communicates with the groove space as the flow path downstream side space 12a described above. In other words, the liquid outflow port 32a and the flow path downstream space 12a constitute a part of the liquid flow path 2a in the housing 2.

Therefore, the liquid flow path 2a in the housing 2 of the present embodiment is constituted by the liquid inflow port 23a, the flow path upstream side space 11a, the flow path downstream side space 12a, and the liquid outflow port 32a. The liquid flowing in from the liquid inflow port 23a passes through the filtration sheet 3 from the flow path upstream side space 11a, enters the groove space as the flow path downstream side space 12a, and flows to the outside from the liquid outflow port 32a.

The joining member 13 of the present embodiment is located in the gap 60 between the first housing member 11 and the second housing member 12, and is joined to the first housing member 11 and the second housing member 12. In other words, the first housing member 11 and the second housing member 12 are joined by the joining member 13. Accordingly, the gap 60 between the first housing member 11 and the second housing member 12 is sealed from the outside. As a result, the liquid flow path 2a can be sealed. That is, the joining member 13 according to the present embodiment is disposed in the gap 60, thereby achieving both joining of the first housing member 11 and the second housing member 12 and sealing of the gap 60.

Specifically, the joining member 13 according to the present embodiment is interposed between the outer edge portion 21c of the top plate portion 21 of the first housing member 11 and the outer edge portion 31c of the main body plate portion 31 of the second housing member 12. More specifically, the joining member 13 according to the present embodiment is disposed over an entire region in a circumferential direction in an annular groove including the gap 60. The annular groove includes the outer edge portion 21c of the top plate portion 21 of the first housing member 11, the annular protruding portion 22 of the first housing member 11, and the outer edge portion 31c of the main body plate portion 31 of the second housing member 12. Accordingly, the gap 60 is sealed by the joining member 13 over the entire region in the circumferential direction.

The first housing member 11, the second housing member 12, and the joining member 13 according to the present embodiment are made of a resin material. The first housing member 11, the second housing member 12, and the joining member 13 are joined by welding such as fusion. In this way, after the first housing member 11 and the second housing member 12 are molded, the gap 60 is filled with a molding material and solidified, and thereby the joining member 13 capable of achieving both the joining of the first housing member 11 and the second housing member 12 and the sealing of the gap 60 can be molded. Specifically, the first housing member 11 and the second housing member 12 are melted by heat generated by the molding material of the joining member 13 and are fusion-bonded to the joining member 13, and the gap 60 is sealed.

Examples of the material of the first housing member 11, the second housing member 12, and the joining member 13 include various resin materials such as polyolefins such as polyethylene, polypropylene, and ethylene-propylene copolymer; ethylene-vinyl acetate copolymer (EVA); polyvinyl chloride; polyvinylidene chloride; polystyrene; polyamide; polyimide; polyamideimide; polycarbonate; poly-(4-methylpentene-1); ionomer; acrylic resin; polymethyl methacrylate; acrylonitrile-butadiene-styrene copolymer (ABS resin); acrylonitrile-styrene copolymer (AS resin); butadiene-styrene copolymer; polyesters such as polyethylene terephthalate (PET), polybutylene terephthalate (PBT), and polycyclohexane terephthalate (PCT); polyether; polyether ketone (PEK); polyether ether ketone (PEEK); polyether imide; polyacetal (POM); polyphenylene oxide; modified polyphenylene oxide; polysulfone; polyethersulfone; polyphenylene sulfide; polyarylate; aromatic polyester (liquid crystal polymer); polytetrafluoroethylene; polyvinylidene fluoride; and other fluorine-based resins.

Although resin materials constituting the first housing member 11, the second housing member 12, and the joining member 13 according to the present embodiment can be appropriately selected from the various resin materials listed above, for example, it is preferable to use the same material such as polycarbonate. In this way, joining strength of the welding of the first housing member 11, the second housing member 12, and the joining member 13 can be increased.

In this way, the joining member 13 according to the present embodiment joins the first housing member 11 and the second housing member 12 by welding the first housing member 11 with the second housing member 12. Alternatively, the configuration thereof is not particularly limited as long as the first housing member 11 and the second housing member 12 are joined and the gap 60 can be sealed. However, as in the present embodiment, the joining member 13 is located in the gap 60 between the first housing member 11 and the second housing member 12, and is joined to the first housing member 11 and the second housing member 12, and thereby the housing 2 can be easily downsized compared with a configuration in which a joining member is provided outside the gap 60.

Although the entire joining member 13 according to the present embodiment is disposed in the annular groove including the gap 60, a part of the joint member 13 may protrude from the annular groove.

As described above, the housing 2 according to the present embodiment includes the first housing member 11, the second housing member 12, and the joining member 13 described above. Alternatively, a member other than the above members may be further provided.

Specific shapes of the first housing member 11, the second housing member 12, and the joining member 13 are not limited to the shapes described above, and may be different shapes. For example, in the present embodiment, the first housing member 11 defines the liquid inflow port 23a of the liquid flow path 2a. The second housing member 12 defines the liquid outflow port 32a of the liquid flow path 2a. Alternatively, the first housing member may define the liquid outflow port, and the second housing member may define the liquid inflow port. One of the first housing member 11 and the second housing member 12 alone may define the liquid inflow port and the liquid outflow port. However, when the filtration sheet 3 is sandwiched between the first housing member 11 and the second housing member 12 as in the present embodiment, it is preferable that the first housing member defines one of the liquid inflow port and the liquid outflow port of the liquid flow path, and the second housing member defines the other one of the liquid inflow port and the liquid outflow port of the liquid flow path. In this way, the configuration of the housing 2 and the path configuration of the liquid flow path 2a defined by the housing 2 can be simplified.

Furthermore, in the present embodiment, the first housing member 11 includes the protruding portion 22 that sandwiches the filtration sheet 3, and the second housing member 12 does not include the protruding portion that sandwiches the filtration sheet 3. Alternatively, the present disclosure is not limited to the configuration. That is, instead of or in addition to the first housing member 11 including the protruding portion 22, the second housing member 12 may include a protruding portion that sandwiches the filtration sheet 3. Further, both the first housing member 11 and the second housing member 12 may be not include the protruding portion that sandwiches the filtration sheet 3. However, as in the present embodiment, at least one member of the first housing member 11 and the second housing member 12 preferably includes a protruding portion protruding toward the other member. In this way, the filtration sheet 3 can be fixed more firmly. Details of the above will be described later.

Further, in the present embodiment, each of the first housing member 11 and the second housing member 12 is formed by one component. Alternatively, the present disclosure is not limited to this configuration, and each of the first housing member 11 and the second housing member 12 may be formed by combining two or more components.

[Filtration Sheet 3]

The filtration sheet 3 according to the present embodiment is a hydrophilic filter having a substantially circular external shape. As the hydrophilic filter as the filtration sheet 3, for example, a hydrophilic porous membrane or a hydrophilic nonwoven fabric can be used. Examples of the material of the filtration sheet 3 include hydrophilic materials such as polysulfone, cellulose acetate, and nitrocellulose. The filtration sheet 3 may be formed by hydrophilizing a hydrophobic filter made of a hydrophobic material such as polypropylene, polyethylene, polyester, or polytetrafluoroethylene.

The filtration sheet 3 according to the present embodiment has the substantially circular external shape. The filtration sheet 3 according to the present embodiment includes a sandwiched portion 41 sandwiched by the first housing member 11 and the second housing member 12, a liquid passage portion 42 located on a radially inward side of the sandwiched portion 41, and an outer edge portion 43 extending on a radially outward side of the sandwiched portion 41.

The sandwiched portion 41 according to the present embodiment is a part of the filtration sheet 3, in which the sandwiched portion 41 is in contact with the distal end surface of the annular protruding portion 22 of the first housing member 11 and the upper surface of the outer edge portion 31c of the main body plate portion 31 of the second housing member 12. The sandwiched portion 41 is sandwiched between the distal end surface of the annular protruding portion 22 and the upper surface of the outer edge portion 31c. That is, the filtration sheet 3 according to the present embodiment is sandwiched between the first housing member 11 and the second housing member 12 at a position of the protruding portion 22. In this way, by sandwiching the filtration sheet 3 at the position of the protruding portion 22, it is possible to narrow a radial range of the sandwiched portion 41 of the filtration sheet 3. Therefore, a compressive force applied from the first housing member 11 and the second housing member 12 to the sandwiched portion 41 of the filtration sheet 3 is less likely to be dispersed, and the filtration sheet 3 can be fixed more firmly between the first housing member 11 and the second housing member 12.

The liquid passage portion 42 according to the present embodiment is located on an inner side relative to the sandwiched portion 41 in a plan view of the filtration sheet 3 as viewed in the thickness direction A. The liquid passage portion 42 is a part that is located in the liquid flow path 2a and removes the foreign matters in the passing liquid. The liquid passage portion 42 of the present embodiment is supported by the top portions of the plurality of ribs 31a provided on an upper surface of the central portion 31b of the main body plate portion 31 of the second housing member 12. The liquid filtered through the liquid passage portion 42 of the filtration sheet 3 from the flow path upstream side space 11a of the liquid flow path 2a defined by the first housing member 11 enters the groove space between the plurality of ribs 31a as the flow path downstream side space 12a defined by the second housing member 12.

The outer edge portion 43 according to the present embodiment is located on an outer side relative to the sandwiched portion 41 in the plan view of the filtration sheet 3 as viewed in the thickness direction A. In other words, the first housing member 11 and the second housing member 12 according to the present embodiment do not sandwich the outer edge 3a of the filtration sheet 3 but sandwich the filtration sheet 3 at a position on an inner side relative to the outer edge 3a. Therefore, the filtration sheet 3 according to the present embodiment includes the outer edge portion 43 extending on a radially outer side relative to the sandwiched portion 41.

The outer edge portion 43 according to the present embodiment is joined to the joining member 13. Specifically, the outer edge portion 43 according to the present embodiment is located between a lower surface of the outer edge portion 21c of the top plate portion 21 of the first housing member 11 and the upper surface of the outer edge portion 31c of the main body plate portion 31 of the second housing member 12. In a plan view in the thickness direction A, the outer edge 3a of the filtration sheet 3 does not protrude outward in the sheet extending direction B beyond an outer edge 21d of the top plate portion 21 of the first housing member 11 and an outer edge 31d of the main body plate portion 31 of the second housing member 12. Also, the joining member 13 according to the present embodiment is not only located in the gap 60 on the outer side relative to the outer edge 3a of the filtration sheet 3 in the sheet extending direction B, but a part of the joining member 13 also enters from the gap 60 to the inner side relative to the outer edge 3a of the filtration sheet 3 in the sheet extending direction B. Accordingly, the joining member 13 according to the present embodiment is joined by welding not only to the first housing member 11 and the second housing member 12, but also to the outer edge portion 43 of the filtration sheet 3. In this way, the joining member 13 is joined not only to the first housing member 11 and the second housing member 12, but also to the outer edge portion 43 of the filtration sheet 3, and thereby the filtration sheet 3 can be fixed more firmly.

As shown in FIGS. 2 and 3, the joining member 13 according to the present embodiment is welded to an upper surface and an outer peripheral end surface of the outer edge portion 43 of the filtration sheet 3 on the first housing member 11 side. Alternatively, the welding position is not particularly limited as long as the joining member 13 is welded to at least one of the upper surface, the outer peripheral end surface, and a lower surface of the outer edge portion 43 of the filtration sheet 3.

In the filtration device 1 according to the present embodiment, the single-layer filtration sheet 3 is sandwiched by the first housing member 11 and the second housing member 12. Alternatively, the present disclosure is not limited to this configuration, and for example, a plurality of stacked filtration sheets 3 may be sandwiched by the first housing member 11 and the second housing member 12.

[Ventilation Sheet 4]

The ventilation sheet 4 according to the present embodiment covers the opening portion 21a defined by the first housing member 11. The gas in the liquid flow path 2a can be discharged from the ventilation sheet 4. More specifically, the ventilation sheet 4 is attached to the lower surface of the top plate portion 21 of the first housing member 11 on the liquid flow path 2a side in a manner of covering the opening portion 21a. The ventilation sheet 4 can be attached to the lower surface of the top plate portion 21 by various methods, for example, welding by heat sealing or the like, or adhesion by an adhesive or the like.

The ventilation sheet 4 is a hydrophobic filter. The ventilation sheet 4 has water impermeability, and allows the gas to flow out from the opening portion 21a and prevents the liquid from flowing out from the opening portion 21a. As the ventilation sheet 4, for example, a hydrophobic porous membrane or a hydrophobic nonwoven fabric can be used. Examples of the material of the ventilation sheet 4 include hydrophobic materials such as polypropylene, polyethylene, polysulfone, polyacrylonitrile, polytetrafluoroethylene, and cellulose acetate.

Next, an infusion set 110 including the filtration device 1 of the present embodiment will be described with reference to FIG. 4.

Figure 4:
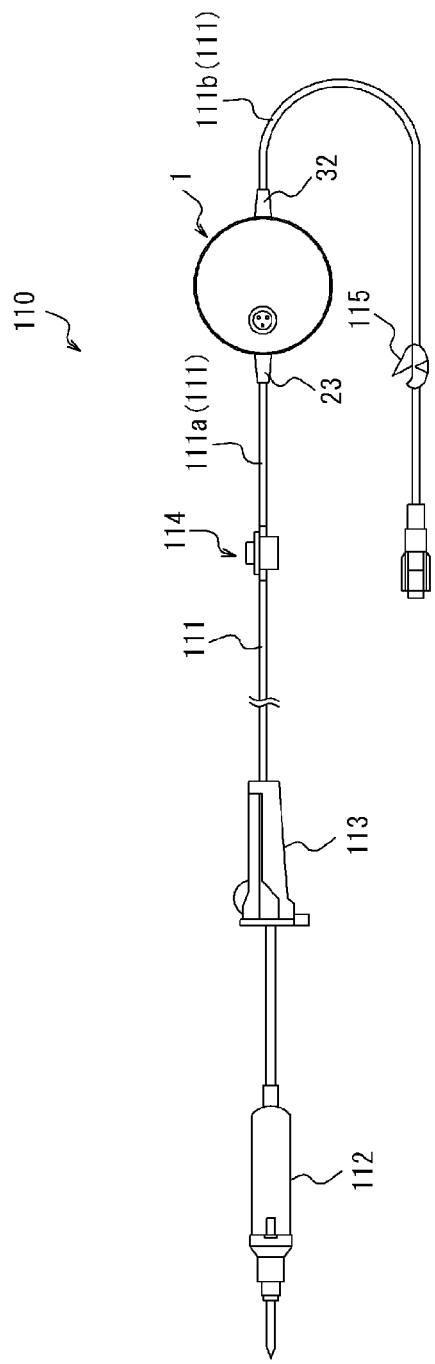
FIG. 4 is a diagram showing an infusion set including the filtration device shown in FIG. 1.

The infusion set 110 can form an infusion line connecting an infusion bag (not shown in FIG. 4) to an indwelling needle (also not shown in FIG. 4). Specifically, the infusion set 110 includes a plurality of infusion tubes 111, a drip chamber 112 capable of visually recognizing a flow rate of an infusion agent supplied from the infusion bag, a clamp 113 that adjusts the flow rate of the infusion agent in the infusion tube 111, the filtration device 1, a connector 114 that connects the infusion tubes 111, and a one-touch clamp 115 that blocks the infusion tubes 111.

In the infusion set 110 shown in FIG. 4, the inflow port portion 23 of the filtration device 1 is liquid-tightly connected to a first infusion tube 111a on the flow path upstream side. The outflow port portion 32 of the filtration device 1 is liquid-tightly connected to a second infusion tube 111b on the flow path downstream side. Accordingly, the liquid in the infusion bag flows from a hollow portion of the first infusion tube 111a into the liquid flow path 2a of the filtration device 1, is filtered by the filtration sheet 3 (see FIGS. 2 and 3), flows out to a hollow portion of the second infusion tube 111b, and is sent to the indwelling needle.

A position of the filtration device 1 in the infusion set 110 is not limited to a position shown in FIG. 4. Although in FIG. 4, the filtration device 1 is disposed on the flow path downstream side relative to the connector 114, the filtration device may be disposed on the flow path upstream side relative to the connector 114, for example.

The infusion set 110 shown in FIG. 4 includes the plurality of infusion tubes 111, the drip chamber cartridge 112, the clamp 113, the filtration device 1, the connector 114, and the one-touch clamp 115. Alternatively, a configuration is not limited to the configuration in FIG. 4 as long as the configuration includes at least one infusion tube 111 and the filtration device 1. Therefore, for example, an infusion set that does not include the connector 114 may be used.

The filtration device according to the present disclosure is not limited to the specific configuration in the embodiment described above, and various modifications and changes can be made without departing from the scope of the claims. Although a filtration device 1 for infusion has been described in the above embodiment, the filtration device according to the present disclosure can be applied to a filtration device for hemodialysis and a filtration device for removing white blood cells as described above. A method for manufacturing the filtration device 1 described above is not particularly limited, and the filtration device 1 can be manufactured using die slide molding, for example.

REFERENCE NUMERAL LIST

1: filtration device
2: housing
2a: liquid flow path
3: filtration sheet
3a: outer edge of filtration sheet
4: ventilation sheet
11: first housing member
11a: flow path upstream side space
12: second housing member
12a: flow path downstream side space
13: joining member
21: top wall portion
21a: opening portion
21b: central portion
21c: outer edge portion
21d: outer edge
22: protruding portion
23: inflow port portion
23a: liquid inflow port
31: main body plate portion
31a: rib
31b: central portion
31c: outer edge portion
31d: outer edge
32: outflow port portion
32a: liquid outflow port
41: sandwiched portion
42: liquid passage portion
43: outer edge portion
60: gap
110: infusion set
111: infusion tube
111a: first infusion tube
111b: second infusion tube
112: drip chamber
113: clamp
114: connector
115: one-touch clamp
A: thickness direction of filtration sheet
B: sheet extending direction of filtration sheet

The invention claimed is:

1. A filtration device comprising:
a housing that defines a liquid flow path, the housing comprising:
a first housing member comprising:
a top plate portion,
an annular protruding portion protruding from the top plate portion, and
an inflow port portion protruding radially outward from the annular protruding portion and defining a liquid inflow port of the liquid flow path, wherein the top plate portion includes a top plate central portion located inward of the annular protruding portion, and a top plate outer edge portion located outward of the annular protruding portion;

a second housing member comprising:

a main body plate portion, and an outflow port portion protruding from the main body plate portion and defining a liquid outflow port of the liquid flow path, wherein the main body plate portion includes a main body plate central portion that faces the top plate central portion, and a main body plate outer edge portion located outward of the main body plate central portion, and a joining member that is located in a gap between the top plate outer edge portion and the main body plate outer edge portion, wherein the joining member joins the first housing member and the second housing member; wherein the joining member is in direct contact with the top plate outer edge portion and the joining member is in direct contact the main body plate outer edge portion; and a filtration sheet that separates the liquid flow path into a flow path upstream side and a flow path downstream side, wherein the filtration sheet is sandwiched by a surface of the annular protruding portion of the first housing member and a surface of the outer edge portion of the second housing member.

2. The filtration device according to claim 1, wherein:
the top plate portion has a substantially circular flat external shape.

3. The filtration device according to claim 1, wherein:
the top plate portion defines an opening portion configured to discharge a gas in the liquid flow path; and
the filtration device further comprises a ventilation sheet that covers the opening portion.

4. The filtration device according to claim 1, wherein:
the main body plate portion has a substantially circular flat external shape.

5. The filtration device according to claim 1, wherein:
the main body plate central portion is formed with a plurality of ribs, and the outer edge portion of the main body plate portion is formed with no ribs.

6. The filtration device according to claim 5, wherein:
the filtration sheet is supported by top portions of the plurality of ribs.

7. The filtration device according to claim 6, wherein:
the plurality of ribs are substantially parallel to each other.

8. The filtration device according to claim 1, wherein:
the joining member is joined to an outer edge portion of the filtration sheet.

* * * * *